United States Patent [19]

Berg

[11] Patent Number: 4,975,158
[45] Date of Patent: Dec. 4, 1990

[54] RECOVERY OF GLYCERINE FROM POLYOLS BY AZEOTROPIC DISTILLATION

[75] Inventor: Lloyd Berg, 1314 S. Third Ave., Bozeman, Mont. 59715

[73] Assignee: Lloyd Bert, Bozeman, Mont.

[21] Appl. No.: 507,121

[22] Filed: Apr. 6, 1990

Related U.S. Application Data

[62] Division of Ser. No. 457,868, Dec. 27, 1989, Pat. No. 4,935,102.

[51] Int. Cl.⁵ .......................... B01D 3/36; C07C 29/82
[52] U.S. Cl. ......................................... 203/63; 203/68; 203/69; 203/70; 568/621; 568/869
[58] Field of Search ....................... 203/62, 63, 68, 69, 203/70; 568/869, 868, 621

[56] References Cited

U.S. PATENT DOCUMENTS

| | | | |
|---|---|---|---|
| 2,865,819 | 12/1958 | Hagemeyer et al. | 203/69 |
| 3,809,724 | 5/1974 | Golden | 203/69 |
| 3,847,754 | 11/1974 | Oliver | 568/621 |
| 3,859,368 | 1/1975 | Kollar | 203/68 |
| 4,021,311 | 5/1977 | Becker | 203/69 |
| 4,057,471 | 11/1977 | Chueh | 203/69 |
| 4,655,879 | 4/1987 | Brockmann et al. | 568/869 |

Primary Examiner—Wilbur Bascomb

[57] ABSTRACT

Glycerine cannot be easily separated from triethylene glycol and 1,2,4-butanetriol by atmospheric or reduced pressure distillation because of the closeness of their boiling points. Glycerine can be readily separated from triethylene glycol and 1,2,4-butanetriol by azeotropic distillation. Typical effective agents are m-xylene, dipentene and 2-methoxyethyl ether.

2 Claims, No Drawings

RECOVERY OF GLYCERINE FROM POLYOLS BY AZEOTROPIC DISTILLATION

This application is a division of Application Serial No. 07/457,868 filed Dec. 27, 1989 now U.S. Pat. No. 4,935,102.

FIELD OF THE INVENTION

This invention relates to a method for separating glycerine from polyols using certain organic compounds as the agent in azeotropic distillation.

DESCRIPTION OF PRIOR ART

Azeotropic distillation is the method of separating close boiling compounds from each other by carrying out the distillation in a multiplate rectification column in the presence of an added liquid, said liquid forming an azeotrope with one or both of the compounds to be separated. Its presence on each plate of the rectification column alters the relative volatility in a direction to make the separation on each plate greater and thus require either fewer plat to effect the same separation or make possible a greater degree of separation with the same number of plates. The azeotrope forming agent is introduced with the feed to a continuous column. The azeotrope forming agent the more volatile component are taken off as overhead product and the less volatile component comes off as bottoms product. The usual methods of separating the azeotrope former from the more volatile component are cooling and phase separation or solvent extraction.

In the hydrocracking of higher carbohydrates such as glucose, sorbitol or sucrose, the molecule is broken into fragments of lower molecular weight to form compounds which belong to the glycol or polyol family. Some of the resulting polyols boil so close to one another that their separation by ordinary rectification is difficult. The relative volatility is so low that a large number of theoretical plates are required to produce high purity polyols.

For instance, three of the close boiling polyols encountered in this process are triethylene glycol, b.p.=285° C., glycerine, b.p. =290° C. and 1,2,4-butanetriol, b.p.=190/18 mm.

TABLE 1

| Plates Required To Effect Separation In 99% Purity | | |
|---|---|---|
| Relative Volatility | Theoretical Plates | Actual Plates, 75% Efficiency |
| 1.25 | 41 | 55 |
| 1.35 | 31 | 42 |
| 1.45 | 25 | 34 |
| 1.50 | 23 | 31 |
| 1.70 | 18 | 24 |
| 1.80 | 16 | 21 |

The difficulty of separating these one from another by rectification can be shown by the data presented in Table 1. Table 1 shows that rectification of glycerine from triethylene glycol in 99% purity requires 55 actual plates. Using azeotropic distillation with an agent yielding a relative volatility of 1.8 would require only 21 actual plates. Thus, azeotropic distillation would be an attractive method of effecting the separation two polyols if agents can be found that (1) will increase the relative volatility of glycerine to triethylene glycol and (2) are easy to recover from the glycerine.

Azeotropic distillation typically requires from one to five parts as much agent as triethylene glycol being boiled up in the column which increases the heat requirement as well as larger diameter plates to accommodate the increased liquid and vapor in the column.

The catalytic hydrocracking of sorbitol gave a mixture of polyols having the composition shown in Table 2. The principal products were

TABLE 2

| Polyols Produced By Hydrocracking Of Sorbitol | | |
|---|---|---|
| Compound | Weight Percent | Boiling Point, °C. |
| 2,3-Butanediol | 3.5 | 182 |
| Propylene glycol | 16.5 | 187 |
| 1,2-Butanediol | 2.0 | 192 |
| Ethylene glycol | 25.2 | 198 |
| 1,3-Butanediol | 2.7 | 206 |
| 2,3-Hexanediol | — | 206 |
| 1,2-Pentanediol | — | 210 |
| 1,4-Pentanediol | — | 220 |
| 1,4-Butanediol | 2.1 | 230 |
| 1,5-Pentanediol | 0.1 | 242 |
| Diethylene glycol | 2.2 | 245 |
| 1,6-Hexanediol | — | 250 |
| Triethylene glycol | 2.1 | 285 |
| Glycerine | 38.8 | 290 |
| 1,2,4-Butanetriol | 4.8 | 190/18 mm. |
| | 100.0 | |

16.5% propylene glycol, 25.2% ethylene glycol and 38.8% glycerine. To be of commercial value in most uses, these compounds must be of high purity. Table 2 shows the other polyols that resulted are 3% 2,3-butanediol, 2% 1,2-butanediol, 2.7% 1,3-butanediol, 2.1% 1,4-butanediol, 0.1% 1,5-pentanediol, 2.2% diethylene glycol, 2.1% triethylene glycol and 4.8% 1,2,4-butanetriol. Table 2 also shows how close these minor polyols boil to propylene glycol, ethylene glycol and glycerine. When this mixture was subjected to rectification, either at one atm. or at reduced pressure, separation to high purity compounds could not be attained.

OBJECTIVE OF THE INVENTION

The objective of this invention is to provide a process or method of azeotropic distillation that will enhance the relative volatility of glycerine from triethylene glycol and 1,2,4-butanetriol in their separation in a column. It is a further object of this invention to identify organic compounds which in addition to the above constraints, are stable, can be separated from the glycerine and can be recycled to the azeotropic distillation and reused with little decomposition.

SUMMARY OF THE INVENTION

The objects of this invention are provided by a process for separating glycerine from triethylene glycol & 1,2,4-butanetriol which entails the use of certain organic compounds in an azeotropic distillation process.

DETAILED DESCRIPTION OF THE INVENTION

I have discovered that certain organic compounds will effectively enhance the relative volatility in azeotropic distillation of glycerine from triethylene glycol and 1,2,4-butanetriol when they occur as a close boiling mixture. In the mixture of polyols shown in Table 2, the major products are propylene glycol, ethylene glycol and glycerine. To be of commercial value, these compounds must be obtained in high purity.

TABLE 3

| Agent | Azeo. Temp. | Time hrs. | OVERHEAD | | | BOTTOMS | | | % TEG in Overhead | Relative Gly:TEG | Volatility Gly:124Bu |
|---|---|---|---|---|---|---|---|---|---|---|---|
| | | | % TEG | % Gly | % 124Bu | % TEG | % Gly | % 124Bu | | | |
| o-Xylene | 96 | 1.5 | 53 | 47 | — | 67.4 | 32.6 | — | 20 | 1.8 | |
| Isopropylcyclohexane | 76 | 4 | 5.2 | 94.8 | 0 | 15.5 | 81.1 | 3.4 | 65 | 3.5 | 10+ |
| m-Xylene | 106 | 1.3 | 0.4 | 99.6 | 0 | 11.6 | 86.6 | 1.8 | 10 | 10+ | 10+ |
| 2,2,4-Trimethylpentane | 91 | 1.5 | 2 | 98 | — | 4 | 96 | — | 15 | 2 | |
| Dipentene | 136 | 5 | 1 | 99 | — | 1.8 | 98.2 | — | 33 | 2.5 | |
| 2-Methoxyethylether | 116 | 3 | 6.1 | 93.9 | — | 13.4 | 81.6 | — | 1φ | 2.5 | |

Triethylene glycol and 1,2,4-butanetriol are the polyols boiling closest to glycerine, see Table 1. Table 3 lists the agents found to be effective in separating glycerine from these two polyols. The 1,2,4-butanetriol boiols so much higher than glycerine that it poses no difficulty in separation. The relative volatility is too high to be measured accurately. All the agents listed in Table 3 except 2-mesh oxyethyl ether form two phase azeotropes with glycerine.

WORKING EXAMPLE

EXAMPLE 1

To a four foot rectification column having thirty theoretical plates was charged 20 grams of triethylen glycol, 20 grams of glycerine, 10 grams of 1,2,4-butanetriol and 100 grams of isopropyl cyclohexane. The overhead temperature was 76° C., the bottoms was 165° C. After four hours at total reflux, an overhead sample comprising 35% isopropyl cyclohexane, 65% glycols was taken. The glycol layer composition was 5.2% triethylene glycol, 94.8% glycerine, 0% 1,2,4-butanetriol and the bottom composition was 15.5% triethylene glycol, 81.1% glycerine and 3.4% 1,2,4- butanetriol. This is a relative volatility of glycerine to triethylene glycol of 3.5. These data are shown in Table 3.

I claim:

1. A method for recovering glycerine from a mixture of glycerine, triethylene glycol and 1,2,4-butanetriol which comprises distilling a mixture of glycerine, triethylene glycol and 1,2,4-butanetriol in a rectification column in the presence of an azeotrope forming agent, recovering the glycerine and the azeotrope forming agent as overhead product, condensing the glycerine and the azeotrope forming agent inot tow liquid phases, separating the glycerine from the azeotrope forming agent by decantation of the two liquid phases, obtaining the triethylene glycol and the 1,2,4-butanetriol from the stillpot, wherein said azeotrope forming agent is one material selected from the group consisting of m-xylene, o-xylene, isopropyl cyclohexane, 2,2,4-trimethylpentane, and dipentene.

2. A method for recovering glycerine from a mixture of glycerine, triethylene glycol and 1,2,4-butanetriol which comprises distilling a mixture of glycerine, triethylene glycol and 1,2,4-butanetriol in a rectification column in the presence of 2-methoxyethyl ether as an azeotrope forming agent, recovering the glycerine and the 2-methoxy-ethyl ether as overhead product, condensing the glycerine and the 2-methoxyethyl ether and obtaining the triethylene glycol and the 1,2,4-butanetriol from the stillpot.

* * * * *